US012729197B2

(12) United States Patent
Sirigireddy et al.

(10) Patent No.: US 12,729,197 B2
(45) Date of Patent: Sep. 8, 2026

(54) PROCESS FOR THE PREPARATION OF VENETOCLAX AND ITS POLYMORPHS THEREOF

(71) Applicant: Natco Pharma Limited, Banjara Hills (IN)

(72) Inventors: Balakrishna Reddy Sirigireddy, Banjara Hills (IN); Veeraswamy Balina, Banjara Hills (IN); Sreenivas Rachakonda, Banjara Hills (IN); Veerender Murki, Banjara Hills (IN); Durga Prasad Konakanchi, Banjara Hills (IN); Pulla Reddy Muddasani, Banjara Hills (IN); Venkaiah Chowdary Nannapaneni, Banjara Hills (IN)

(73) Assignee: NATCO PHARMA LIMITED, Hyderabad (IN)

( * ) Notice: Subject to any disclaimer, the term of this patent is extended or adjusted under 35 U.S.C. 154(b) by 1122 days.

(21) Appl. No.: 17/626,078

(22) PCT Filed: Jul. 8, 2020

(86) PCT No.: PCT/IN2020/050594

§ 371 (c)(1),
(2) Date: Jan. 10, 2022

(87) PCT Pub. No.: WO2021/009770

PCT Pub. Date: Jan. 21, 2021

(65) Prior Publication Data

US 2022/0259204 A1 Aug. 18, 2022

(30) Foreign Application Priority Data

Jul. 12, 2019 (IN) ............................ 201941028028

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC .................................................... C07D 471/04
See application file for complete search history.

(56) References Cited

U.S. PATENT DOCUMENTS

| | | | | |
|---|---|---|---|---|
| 8,546,399 | B2 | 10/2013 | Bruncko et al. | |
| 8,722,657 | B2 | 5/2014 | Catron et al. | |
| 9,006,438 | B2 | 4/2015 | Chan et al. | |
| 2014/0275540 | A1* | 9/2014 | Chan .................... | C07D 471/04 560/103 |
| 2019/0185471 | A1* | 6/2019 | Peddi Reddy .......... | A61P 35/02 |

FOREIGN PATENT DOCUMENTS

| | | | |
|---|---|---|---|
| WO | 2011149492 | A1 | 12/2011 |
| WO | 2017063572 | A1 | 4/2017 |
| WO | 2017212431 | A1 | 12/2017 |
| WO | 2018069941 | A2 | 4/2018 |
| WO | 2018157803 | A1 | 9/2018 |

OTHER PUBLICATIONS

Bartlett "Exploiting Chemical Diversity for Drug Discovery" Edited by Paul A Bartlett and Michael Entzeroth, The Royal Society of Chemistry, 2006, pp. 113-118.*

"Find ETDs Home > Thesis Resources > Find ETDs" Online: "https://ndltd.org/thesis-resources/find-etds/" Accessed Jan. 31, 2023.*

Irwin "ZINC—A Free Database of Commercially Available Compounds for Virtual Screening" J. Chem. Inf. Model. 2005, 45, 177-182.*

Kim "PubChem in 2021: new data content and improved web interfaces" Nucleic Acids Research, 2021, vol. 49, Database issue Published online Nov. 5, 2020.*

Stn Registry/Zregistry (CAS Registrysm) Sep. 2016 2 pages.*

* cited by examiner

*Primary Examiner* — Nizal S Chandrakumar
(74) *Attorney, Agent, or Firm* — Dickinson Wright PLLC

(57) ABSTRACT

The present invention relates to a process for the preparation of 4-(4-{[2-(4-chlorophenyl)-4,4dimethylcyclohex-1-en-1-yl]methyl}piperazin-1-yl)-N-({3-nitro-4-[(tetrahydro-2H-pyran-4ylmethyl)amino]phenyl}sulfonyl)-2-(1H-pyrrolo[2,3-b] pyridin-5-yloxy)benzamide) compound of formula-1 which is represented by the following structural formula:

Formula-1

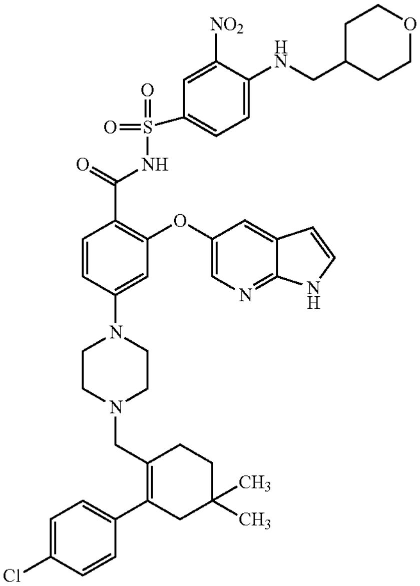

4 Claims, 4 Drawing Sheets

PROCESS FOR THE PREPARATION OF VENETOCLAX AND ITS POLYMORPHS THEREOF

CROSS-REFERENCES TO RELATED APPLICATIONS

This application is a U.S. National Phase Application of PCT International Application No. PCT/IN2020/050594, filed Jul. 8, 2020, which is an International Application of and claims the benefit of priority to Indian Patent Application No. 201941028028, filed Jul. 12, 2019, the entire contents of which are herein incorporated by reference.

FIELD OF THE INVENTION

The present invention relates to a process for the preparation of 4-(4-{[2-(4-chlorophenyl)-4,4dimethylcyclohex-1-en-1-yl]methyl}piperazin-1-yl)-N-({3-nitro-4-[(tetrahydro-2H-pyran-4ylmethyl)amino]phenyl}sulfonyl)-2-(1H-pyrrolo[2,3-b] pyridin-5-yloxy)benzamide) compound of formula-1 which is represented by the following structural formula:

Formula-1

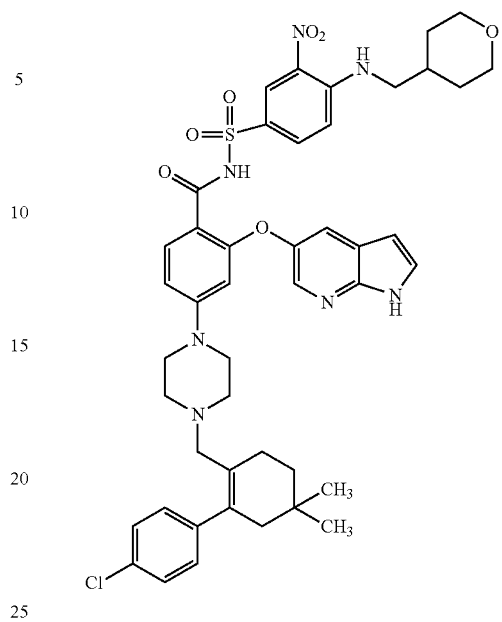

BACKGROUND OF THE INVENTION

Venetoclax is chemically known as 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl) amino]phenyl}sulfonyl)-2-(1H-pyrrolo[2,3-b]pyridin-5-yloxy) benzamide. Venetoclax was developed by Abbvie Inc. and approved by USFDA as VENCLEXTA® tablets which is indicated for the treatment of chronic lymphocytic leukaemia.

PCT publication WO2011149492A1 and its corresponding US equivalent 8546399B2 first disclosed Venetoclax and its pharmaceutical composition. Further, US'399 patent disclosed a process for the preparation of Venetoclax which is schematically represented as below:

Scheme 1

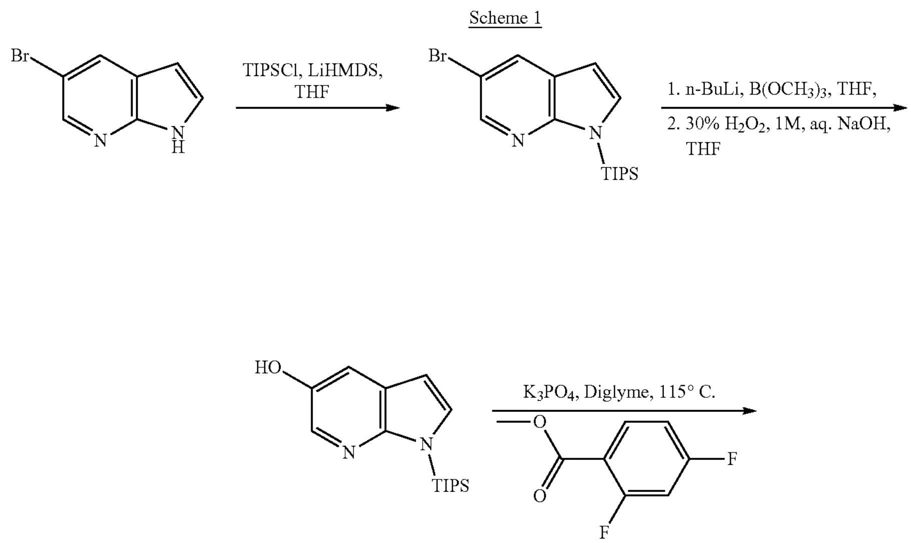

-continued

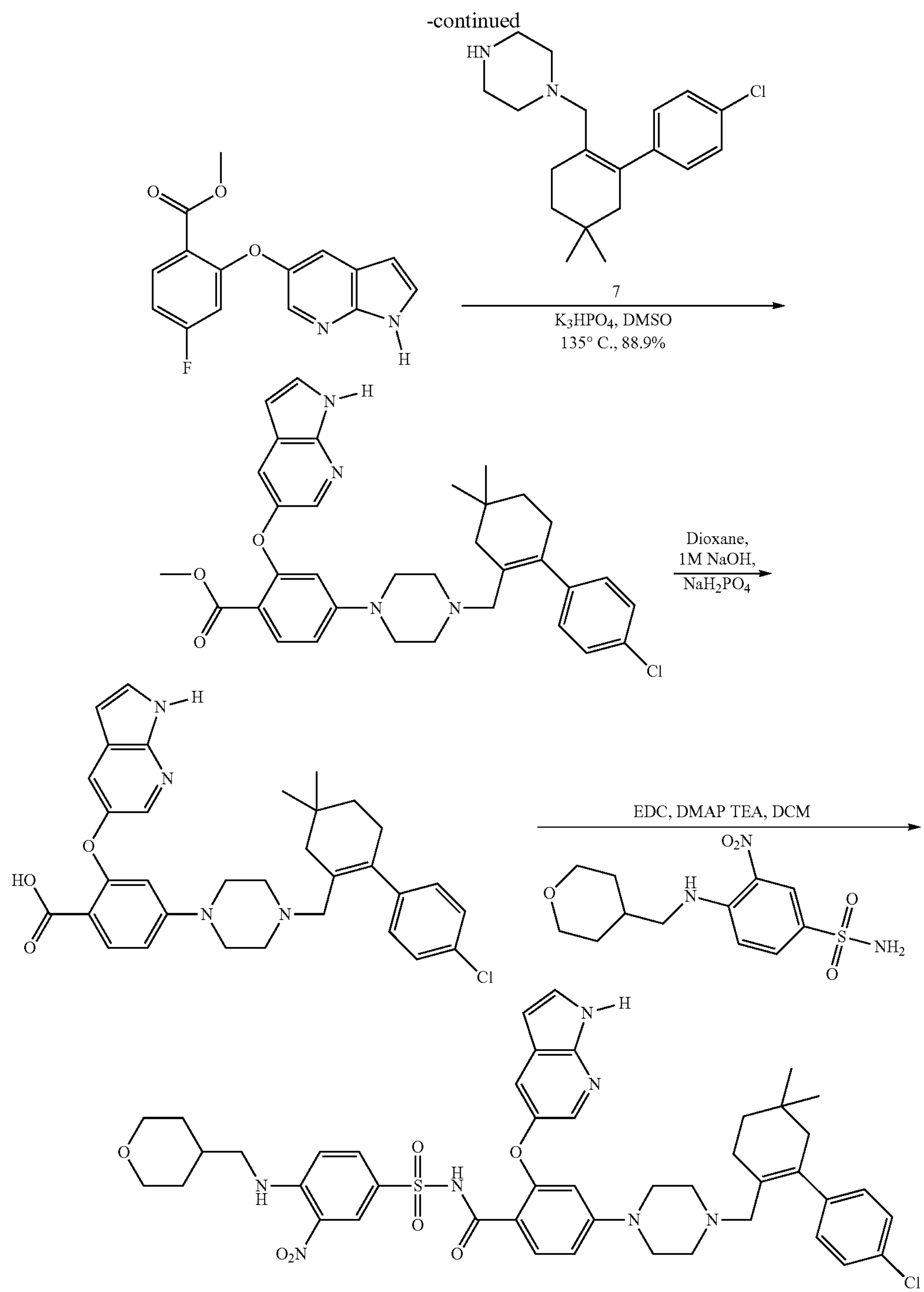

The disadvantage with the above prior art process is, the usage of column chromatographic techniques in the final step for the purification of Venetoclax is commercially not viable. Further, the Venetoclax obtained from the above process resulting very low yields which is commercially not scalable.

U.S. Pat. No. 9,006,438B2 specifically claims the process for preparation of Venetoclax which is schematically represented as below.

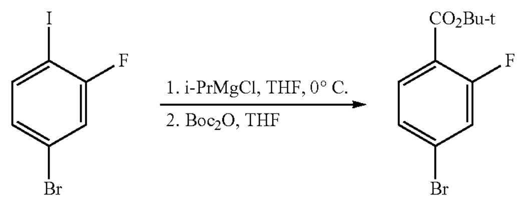
1. i-PrMgCl, THF, 0° C.
2. $Boc_2O$, THF
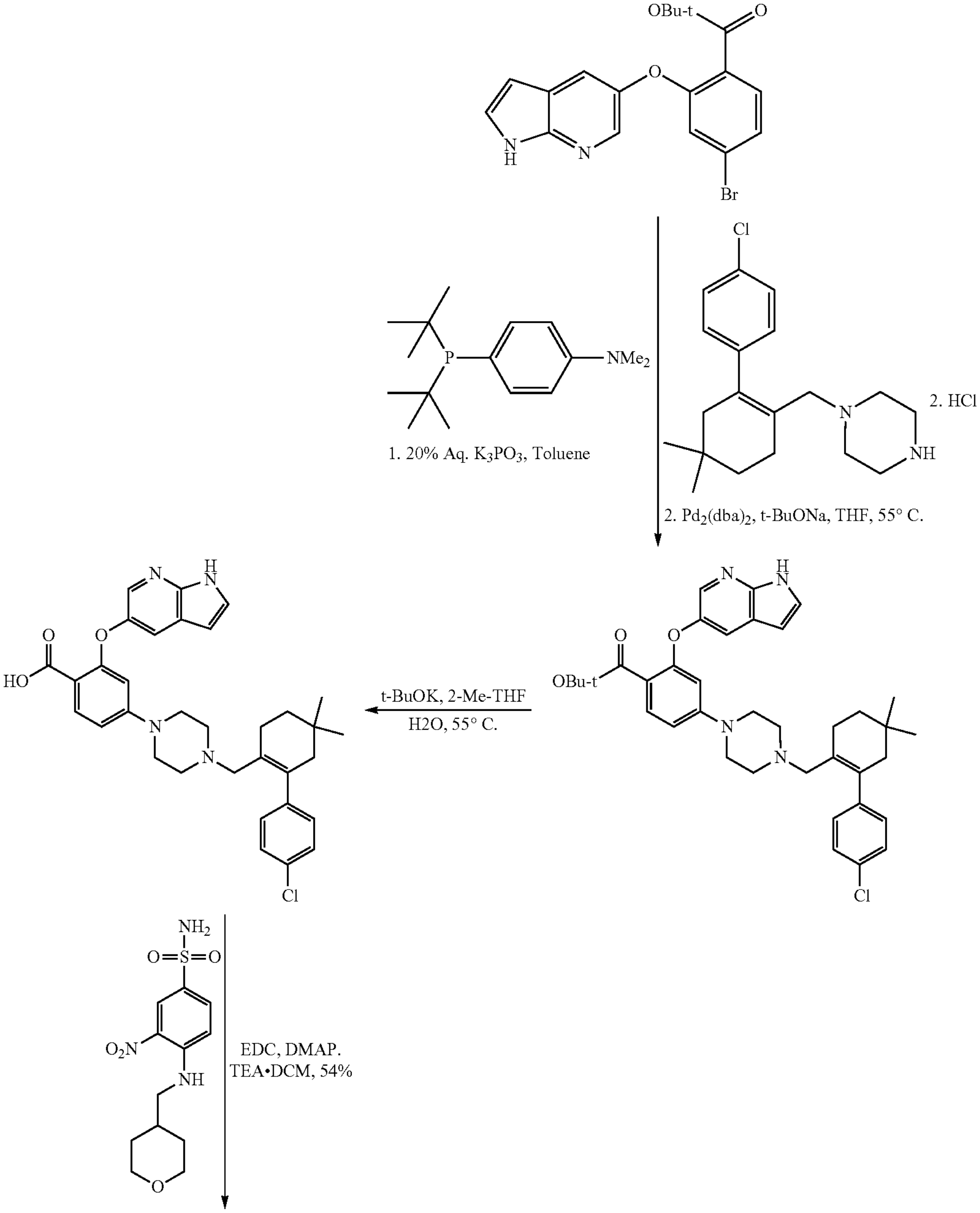
1. t-BuONa, DMF, 45-50° C.
2. Recrystallised in EtOAc, & Heptane 85%
1. 20% Aq. $K_3PO_3$, Toluene
2. HCl
2. $Pd_2(dba)_2$, t-BuONa, THF, 55° C.
t-BuOK, 2-Me-THF
H2O, 55° C.
EDC, DMAP.
TEA•DCM, 54%

-continued

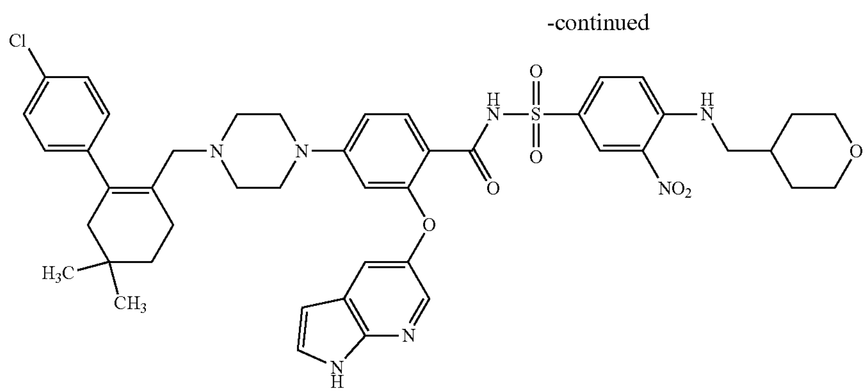

The disadvantage with the above process is the usage of costly & hazardous reagents and reaction conditions which is not suitable for industrial production.

U.S. Pat. No. 8,722,657 B2 describes crystalline forms of Venetoclax free base anhydrates (Form-A & Form-B), free-base hydrates (Form-C & Form-D) and solvates forms of Venetoclax.

PCT publication No. WO2017063572 discloses crystalline forms of Venetoclax such as Form B, Form D, Form F, Form G and its process for preparation.

PCT publication No. WO2018157803A1 discloses crystalline forms of Venetoclax such as CS1,CS2,CS3,CS4,CS5 and CS6.

PCT publication No. WO2017212431 discloses crystalline forms of Venetoclax such as Form RT1, Form RT2, Form RT3, Form RT4 and Form RT5.

PCT publication No. WO2018069941 discloses crystalline forms of Venetoclax such as Form-M1 to Form-M22.

There are disclosures in the art for crystalline and amorphous forms of Venetoclax and the processes for the preparation thereof; however, it is known that the amorphous forms of a number of pharmaceutical substances exhibit different dissolution characteristics and in some cases bioavailability patterns compared to crystalline forms. For some therapeutic indications the bioavailability is one of the key parameters determining the form of the substance to be used in a pharmaceutical formulation.

Therefore, there is a constant need for the novel crystalline and amorphous solid state forms and processes thereof. There also a need of such crystalline forms to enable the preparation of Venetoclax in an amorphous form, wherein any crystalline form, mixture of crystalline forms, mixture of crystalline and amorphous form, solvates or hydrates of Venetoclax can be used as starting material and can be converted into the amorphous form of Venetoclax or amorphous form can be isolated directly from the reaction mixture.

Thus the present invention avoids the usage of expensive reagents and column chromatography techniques which are commercially not viable.

The present invention provides efficient, economically viable, easily scalable process for the preparation of Venetoclax. And also developed a method of producing amorphous form of Venetoclax, which is commercially feasible in large scale production with greater yield, higher purity and good stability.

BRIEF DESCRIPTION OF THE INVENTION

The first aspect of the present invention is to provide a process for the preparation of Venetoclax compound of formula-1.

The second aspect of the present invention is to provide a purification process for Venetoclax compound of formula-1.

DETAILED DESCRIPTION OF THE INVENTION

Figure 1:
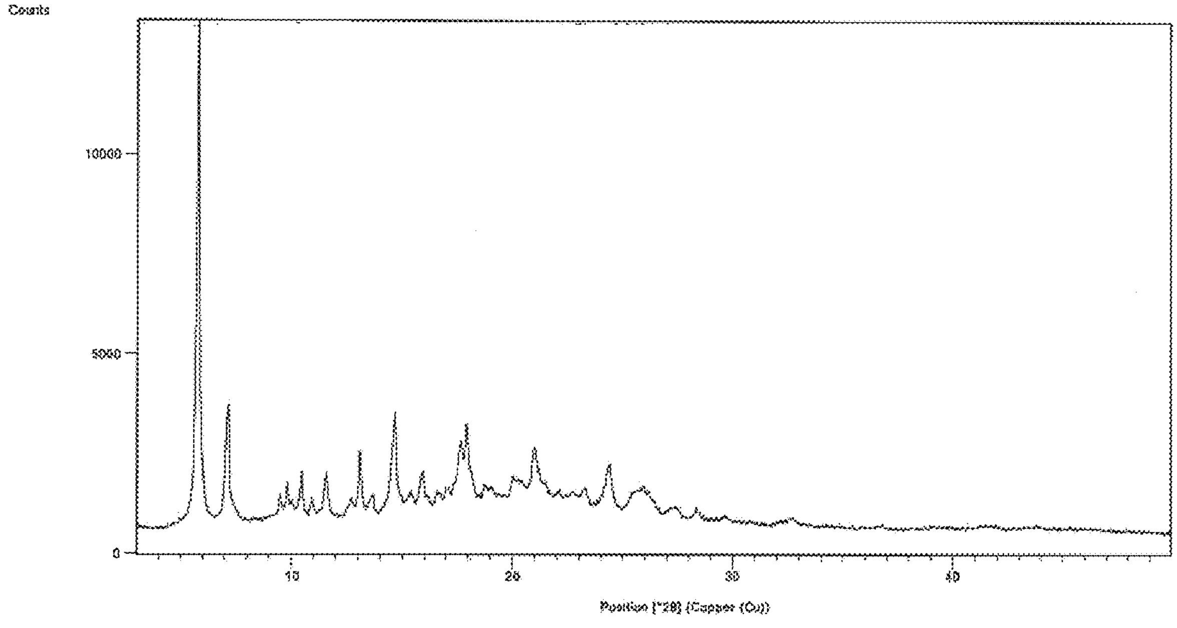
FIG. 1: Illustrates a characteristic PXRD of Venetoclax wet compound of formula-1 obtained according to example-3.

The term "suitable solvent" used in the present invention refers to "hydrocarbon solvents" selected from aliphatic hydrocarbon solvents such as n-hexane, n-heptane, cyclohexane, petroleum ether and aromatic hydrocarbon solvents such as benzene, toluene, xylene and the like; "ether solvents" such as dimethyl ether, diisopropyl ether, diethyl ether, methyl tert-butyl ether, 1,2-dimethoxy ethane, tetrahydrofuran, 1,4-dioxane, monoxime, dioxime and the like; "ester solvents" such as methyl acetate, ethyl acetate, isopropyl acetate, n-butyl acetate and the like; "polar-aprotic solvents such as dimethylacetamide, dimethylformamide, dimethylsulfoxide, N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol and the like; "polar solvents" such as water or mixtures thereof.

As used herein the present invention, the term "anti-solvent" refers to a solvent which is used to precipitate the solid from a solution.

As used herein the present invention the term "suitable base" refers to "alkali metal carbonates" such as sodium carbonate, potassium carbonate, lithium carbonate and the like; "alkali metal bicarbonates" such as sodium bicarbonate, potassium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, sodium tert.butoxide, potassium tert.butoxide, lithium tert.butoxide and the like; alkali metal hydrides such as sodium hydride, potassium hydride, lithium hydride and the like; alkali metal amides such as sodium amide, potassium amide, lithium amide and the like; and organic bases like dimethylamine, diethylamine, diisopropylamine, diisopropylethylamine, diisobutylamine, triethylamine, pyridine, 4-dimethylaminopyridine (DMAP), N-methyl morpholine (NMN), 2,6-lutidine, lithium diisopropylamide; organosilicon bases such as lithium hexamethyldisilazide (LiHMDS), sodium hexamethyldisilazide (NaHMDS), potassium hexamethyldisilazide (KHMDS) or mixtures thereof.

The first aspect of the present invention is to provide a process for the preparation of Venetoclax compound of formula-1, comprising of:

a) Reacting the 4-fluoro-2-(1H-pyrrolo[2,3-b]pyridin-5-yloxy)benzoic acid methyl ester compound of formula-2 with 1-[[2-(4-chlorophenyl)-4,4-dimethyl-cyclohexen-1-yl]methyl]piperazine compound of formula-3 in presence of a suitable organic base in a suitable solvent to provide methyl 4-[4-[[2-(4-chlorophenyl)-4,4-dimethyl-cyclohexen-1-yl]methyl]piperazin-1-yl))-2-(1H-pyrrolo[2,3-b]pyridin-5-yloxy) benzoate compound of formula-4, optionally purifying the compound with a suitable solvent or mixture of solvents, b) treating the obtained compound in-situ with aqueous NaOH in a solvent to provide 4-[4-[[2-(4-chlorophenyl)-4,4-dimethyl-cyclohexen-1-yl]methyl] piperazin-1-yl))-2-(1H-pyrrolo[2,3-b]pyridin-5-yloxy)benzoic acid compound of formula-5, optionally purifying the compound with a suitable solvent or mixture of solvents, c) reacting the compound of formula-5 with 3-nitro-4-((tetrahydro-2H-pyran-4-yl)methylamino)benzene sulfonamide compound of formula-6 in presence of EDC.HCl and DMAP in methylene chloride to provide Venetoclax compound of formula-1, optionally purifying the obtained compound with a suitable solvent or mixture of solvents, d) purifying the Venetoclax compound of formula-1 with a suitable solvent or mixture of solvents to provide pure compound of formula-1.

Wherein, in step-a) the suitable organic base used is selected from dimethylamine, diethylamine, diisopropylamine, diisopropylethylamine, diisobutylamine, triethylamine, pyridine, 4-dimethylaminopyridine (DMAP), N-methyl morpholine (NMM), 2,6-lutidine, lithium diisopropylamide; organosilicon bases such as lithium hexamethyldisilazide (LiHMDS), sodium hexamethyldisilazide (NaHMDS), potassium hexamethyldisilazide (KHMDS) or mixtures thereof in step-a, b & d) the suitable solvent is selected from alcoholic solvents, polar-aprotic solvents, hydrocarbon solvents, nitrile solvents and polar solvents such as water or mixtures thereof;

The preferred embodiment of the present invention provides a process for the preparation of Venetoclax compound of formula-1, comprising of:

a) Reacting the 4-fluoro-2-(1H-pyrrolo[2,3-b]pyridin-5-yloxy)benzoic acid methyl ester compound of formula-2 with 1-[[2-(4-chlorophenyl)-4,4-dimethyl-cyclohexen-1-yl]methyl]piperazine compound of formula-3 in presence of triethylamine in dimethylsulfoxide provides methyl 4-[4-[[2-(4-chlorophenyl)-4,4-dimethyl-cyclohexen-1-yl]methyl]piperazin-1-yl))-2-(1H-pyrrolo[2,3-b]pyridin-5-yloxy) benzoate compound of formula-4, purifying the obtained compound with methanol followed by water, b) treating the obtained compound in-situ with aqueous NaOH in dimethylsulfoxide provides 4-[4-[[2-(4-chlorophenyl)-4,4-dimethyl-cyclohexen-1-yl]methyl]piperazin-1-yl))-2-(1H-pyrrolo[2,3-b]pyridin-5-yloxy)benzoic acid compound of formula-5, purifying the obtained compound with a mixture of toluene and acetonitrile, c) reacting the compound of formula-5 with 3-nitro-4-((tetrahydro-2H-pyran-4-yl)methylamino)benzene sulfonamide compound of formula-6 in presence of EDC.HCl and DMAP in methylene chloride provides Venetoclax compound of formula-1, purifying the obtained compound with a mixture of toluene and acetonitrile, d) purifying the Venetoclax compound of formula-1 with toluene provides pure compound of formula-1.

The second aspect of the present invention is to provide a purification process for Venetoclax compound of formula-1, comprising of:

a) Adding Venetoclax compound of formula-1 in a first solvent, b) heating, stirring, cooling and filtering the reaction mixture, c) adding a suitable second solvent to the filtrate obtained in step-(b), d) heating, stirring, cooling and filtering the reaction mixture, e) adding first solvent to the filtrate obtained in step-(d), f) heating, stirring, cooling the reaction mixture, g) filtering, washing and drying the compound to get the pure Venetoclax compound of formula-1.

Wherein, the suitable first solvent used in step-(a) & (e) is selected from hydrocarbon solvents, preferably aromatic hydrocarbon solvents such as toluene; and the second solvent used in step-(c) is selected from hydrocarbon solvents, nitrile solvents or mixtures thereof.

The preferred embodiment of the invention provides a purification process for Venetoclax compound of formula-1, comprising of:

a) Adding Venetoclax compound of formula-1 in toluene, b) heating, stirring, cooling and filtering the reaction mixture, c) adding a mixture of toluene and acetonitrile to the filtrate obtained in step-(b), d) heating, stirring, cooling and filtering the reaction mixture, e) adding toluene to the filtrate obtained in step-(d), f) heating, stirring, cooling the reaction mixture, g) filtering, washing and drying the compound to get the pure Venetoclax compound of formula-1.

The 4-fluoro-2-(1H-pyrrolo[2,3-b]pyridin-5-yloxy)benzoic acid methyl ester compound of formula-2 and 1-[[2-(4-chlorophenyl)-4,4-dimethyl-cyclohexen-1-yl]methyl]piperazine compound of formula-3 and 3-nitro-4-((tetrahydro-2H-pyran-4-yl)methylamino)benzene sulfonamide compound of formula-6 are prepared from the processes known in the art.

PXRD Method of Analysis:

PXRD analysis of the crystalline forms of Venetoclax were carried out using Panlytical Expert Pro DY3248 X-ray powder diffractometer using Cu-Ka radiation of 10 wavelength 1.5406 A° and at continuous scan speed of 0.03°/min.

The process for the preparation of Venetoclax compound of formula-1 is schematically represented as below:

Scheme-I

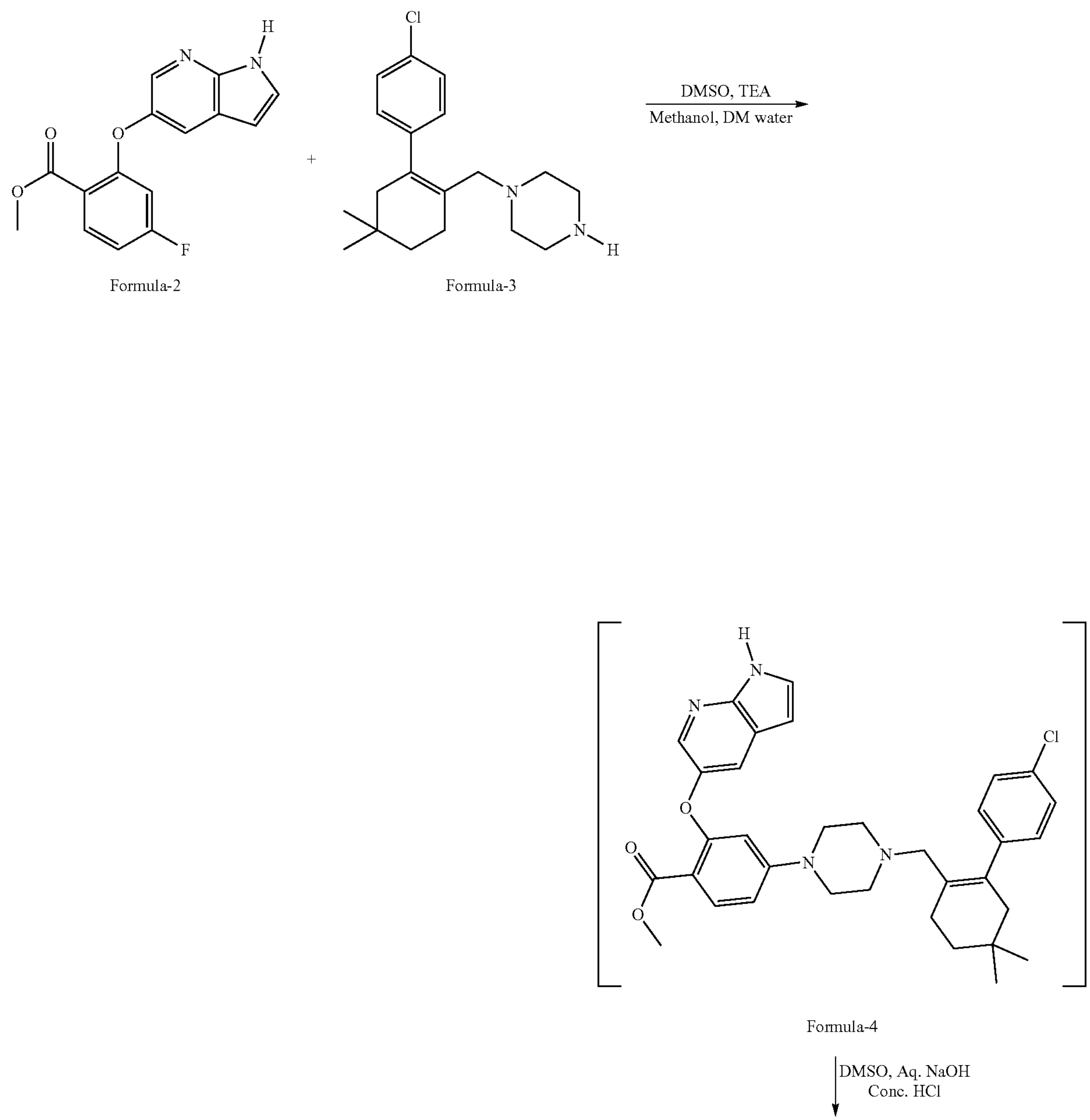

Formula-2

Formula-3

Formula-4

-continued

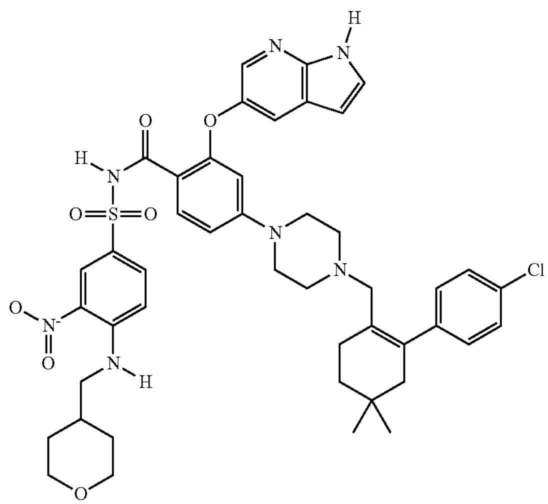

(Venetoclax)
Formula-1

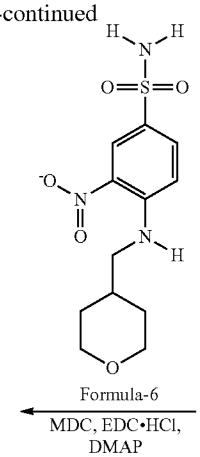

Formula-6

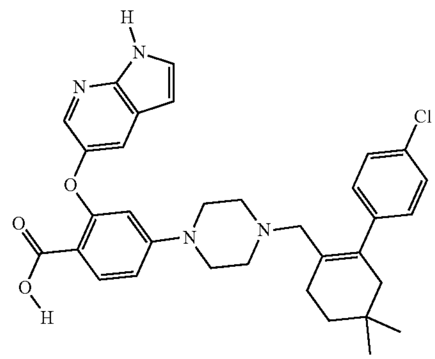

Formula-5

The best mode of carrying out the present invention was illustrated by the below mentioned examples. These examples are provides as illustration only and hence should not be construed as limitation of the scope of the invention.

EXAMPLES

Example-1: Process for the preparation of methyl 4-[4-[[2-(4-chlorophenyl)-4,4-dimethyl-cyclohexen-1-yl]methyl]piperazin-1-yl))-2-(1H-pyrrolo[2,3-b] pyridin-5-yloxy) benzoate(Formula-4)

4-fluoro-2-(1H-pyrrolo[2,3-b]pyridin-5-yloxy)benzoic acid methyl ester(100 g) (Formula-2) and dimethyl sulfoxide (500 mL) were charged into 4N RB Flask and stirred for 10 min at 25-30° C. Charged 1-[[2-(4-chlorophenyl)-4,4-dimethyl-cyclohexen-1-yl]methyl]piperazine (155.8 g) (Formula-3) and triethylamine (106 g) into the reaction mixture and stirred for 10 min at 25-30° C. Heated the reaction mixture to 90-95° C. and stirred for 32-35 hrs. Cooled the reaction mixture temperature to 55-60° C. and charged methanol (3000 mL) and further cooled to 25-30° C. Stirred the reaction mixture for 8-10 hrs at same temperature. Filtered and washed the compound with methanol. Water (1000 ml) was added to the obtained wet compound and stirred the reaction mixture for 60-90 min at 25-30° C. Filtered and washed the wet compound with water to get the title compound. Wet wt: 263 g

Example-2: Process for the preparation of 4-[4-[[2-(4-chlorophenyl)-4,4-dimethyl-cyclohexen-1-yl] methyl]piperazin-1-yl))-2-(1H-pyrrolo[2,3-b]pyridin-5-yloxy) benzoic acid(Formula-5)

The compound of formula-4 obtained from example-1 (225.3 g) and dimethyl sulfoxide (1300 mL) were charged into 4N RB flask and stirred for 10 min at 25-30° C. Sodium hydroxide solution (26.6 g of Sodium hydroxide dissolved in 130 mL of Water) was slowly added to reaction mixture at the same temperature and stirred for 2.5-3.0 hrs. Water (2600 mL) was added to the reaction mixture and maintaining the temperature below 40° C. and not crossing 40° C. The pH of the reaction mixture was adjusted to 5.5 and 6.5 with dilute HCl (Diluted the 70 mL of HCl in 630 mL of Water) at 25-30° C. and stirred for 2-2.5 hrs. Heated the reaction mixture temperature to 40-45° C. and stirred for 20-30 mins. Filtered the compound and washed with water followed by acetonitrile. Mixture of toluene (1300 mL) and acetonitrile (1300 mL) were charged into 4N RB flask and charged above wet material and stirred for 10 mins at 25-30° C. Heated the reaction mixture to 70-75° C. and stirred for 20-30 min. Cooled the reaction mixture to 25-30° C. and stirred for 3-4 hrs. Filtered and washed the compound with a mixture of toluene and acetonitrile and dried to get the title compound. Yield: 82.33 g (64.8% by theory)

Example-3: Process for the preparation of 4-(4-{[2-(4-chlorophenyl)-4,4-dimethylcyclohex-1-en-1-yl] methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide (Venetoclax Formula-1)

Figure 2:
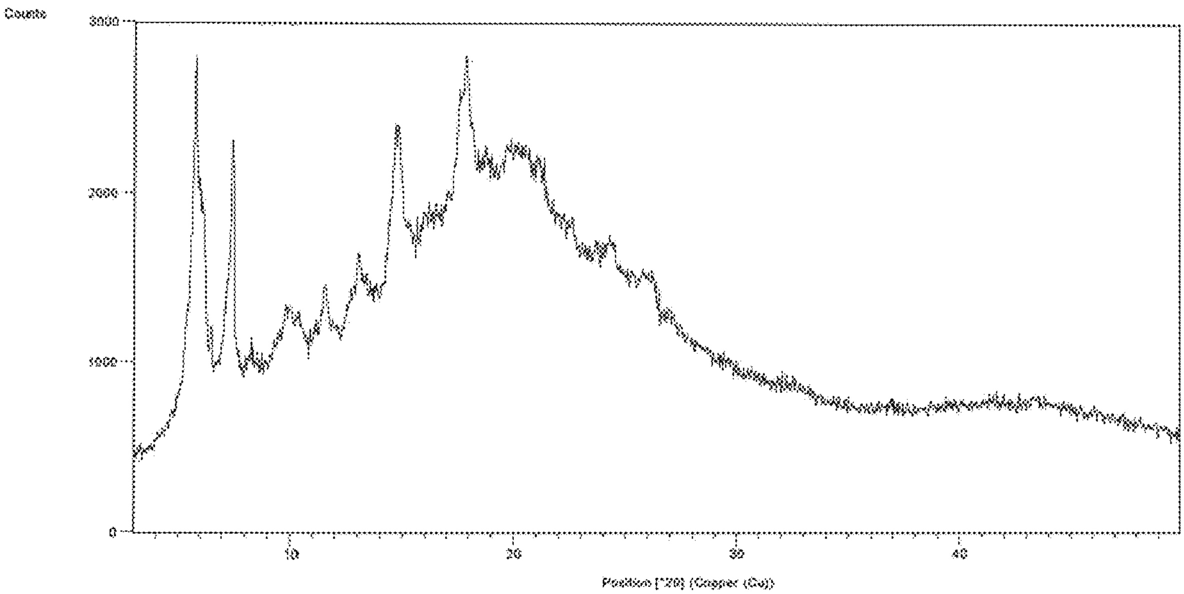
FIG. 2: Illustrates a characteristic PXRD of Venetoclax after drying the compound of formula-1 obtained according to example-3.

The compound of formula-5 obtained from example-2 (70 g) and methylene chloride (1400 mL) were charged into 4N RB flask under nitrogen atmosphere and stirred for 10 min at 25-30° C. Charged DMAP (26.9 g) and 3-nitro-4-((tetrahydro-2H-pyran-4-yl)methylamino)benzene sulfonamide (Formula-6) (38.6 g) and stirred for 10 min at 25-30° C. Charged EDC.HCl (32.8 g) and stirred the reaction mixture for 4-5 hrs at the same temperature. Water (1400 mL) was added to the reaction mixture and stirred for 30 min at 25-30° C. Separated aqueous and organic layers and combined the organic layers washed with acetic acid solution, sodium bicarbonate solution followed by water. The organic layers were distilled completely to get the title compound as crude. Wt: 135.23 g The PXRD of Venetoclax wet compound of formula-1 is illustrated in figure-1 and dry compound is illustrated in figure-2.

Figure 3:
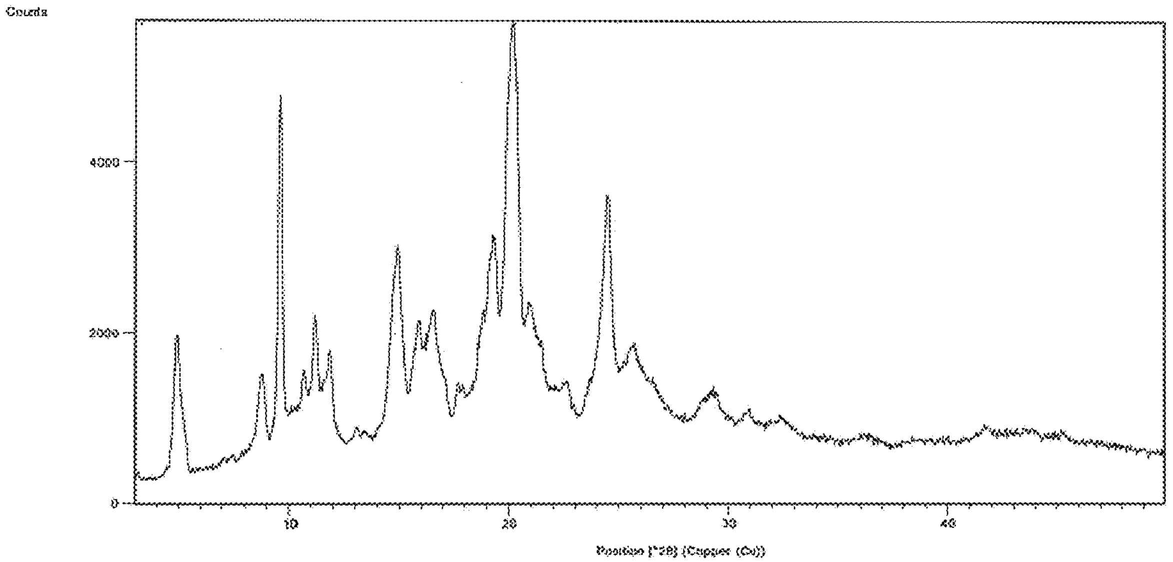
FIG. 3: Illustrates a characteristic PXRD of recrystallized wet compound of Venetoclax (RC-1) obtained according to example-4(a).
Figure 4:
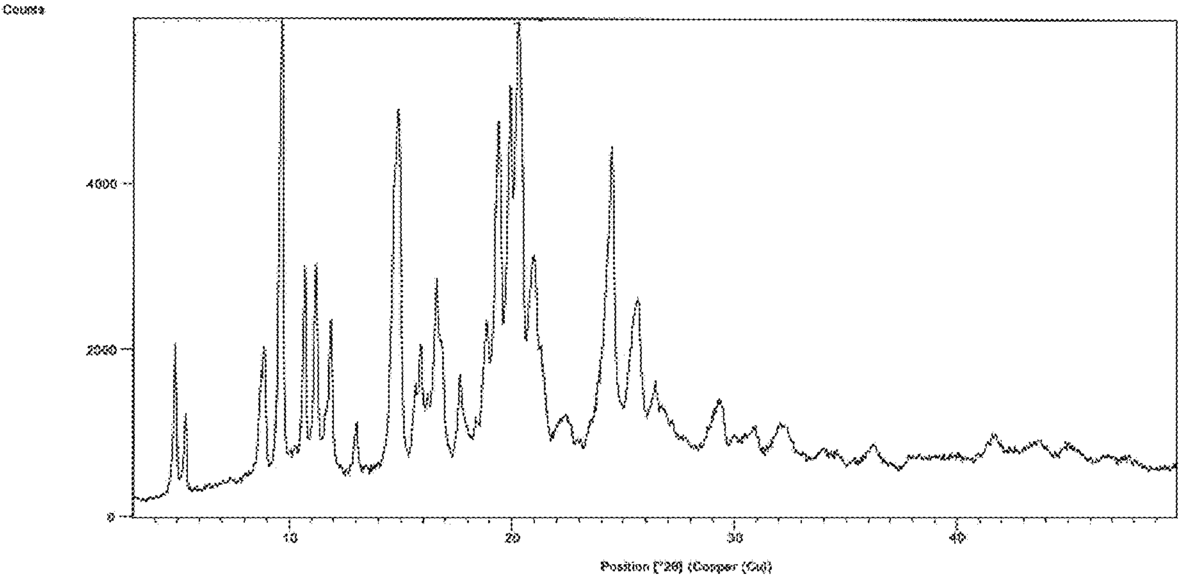
FIG. 4: Illustrates a characteristic PXRD of recrystallized dry compound of Venetoclax (RC-1) obtained according to example-4(a).
Figure 5:
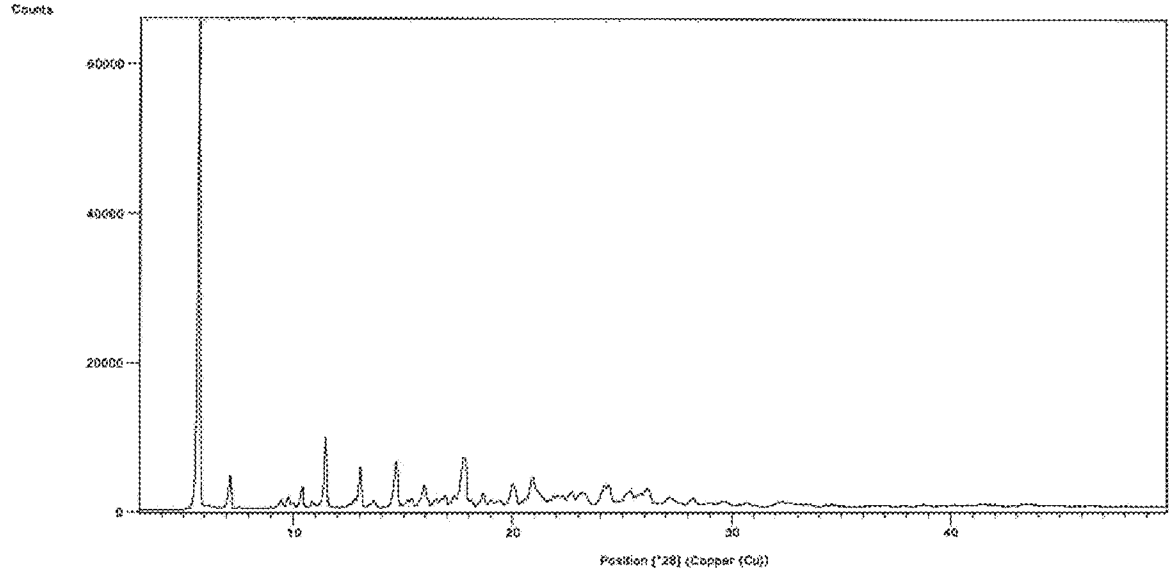
FIG. 5: Illustrates a characteristic PXRD of recrystallized wet compound of Venetoclax (RC-2) obtained according to example-4(b).
Figure 6:
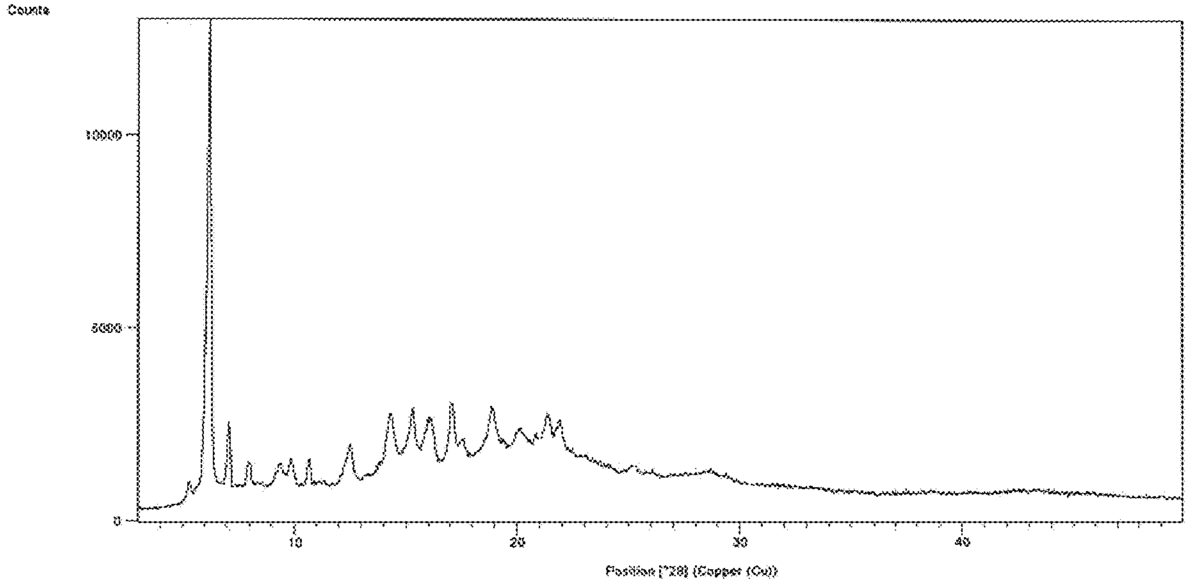
FIG. 6: Illustrates a characteristic PXRD of recrystallized dry compound of Venetoclax (RC-2) obtained according to example-4(b).

Example-4: Purification of Venetoclax Compound of Formula-1 a) Recrystallization in Toluene (RC-1): Charged toluene (1400 mL) and the crude Venetoclax obtained from example-3 into 4N RB flask and heated to 95-100° C. and stirred for 20-30 min. Cooled the reaction mixture temperature to 25-30° C. and stirred for 2.5-3.0 hrs. Filtered and washed the wet compound with toluene to get the Venetoclax compound (RC-1). Wet wt: 122.55 g The PXRD of recrystallized wet compound of Venetoclax (RC-1) is illustrated in figure-3 and dry compound is illustrated in figure-4.

b) Recrystallization in a mixture of Toluene and Acetonitrile (RC-2): Charged a mixture of toluene (350 mL) & acetonitrile (350 mL) and the above wet compound (RC-1) obtained in step-(a) into 4N RB flask and heated to 80-85° C. and stirred for 20-30 min. Cooled the reaction mixture temperature to 25-30° C. and stirred for 2.5-3.0 hrs. Filtered and washed the wet compound with a mixture of toluene and acetonitrile to get the Venetoclax compound (RC-2). Wet wt: 92.7 g The PXRD of recrystallized wet compound of Venetoclax (RC-2) is illustrated in figure-5 and dry compound is illustrated in figure-6.

c) Recrystallization in Toluene: Charged toluene (1400 mL) and the above wet compound (RC-2) obtained in step-(b) into 4N RB Flask and heated to 95-100° C. and stirred for 20-30 min. Cooled the reaction mixture temperature to 25-30° C. and stirred for 2.5-3.0 hrs. Filtered and washed with toluene and dried to get the pure compound of Venetoclax. Yield: 65.71 g (61.73% by theory)

Figure 7:
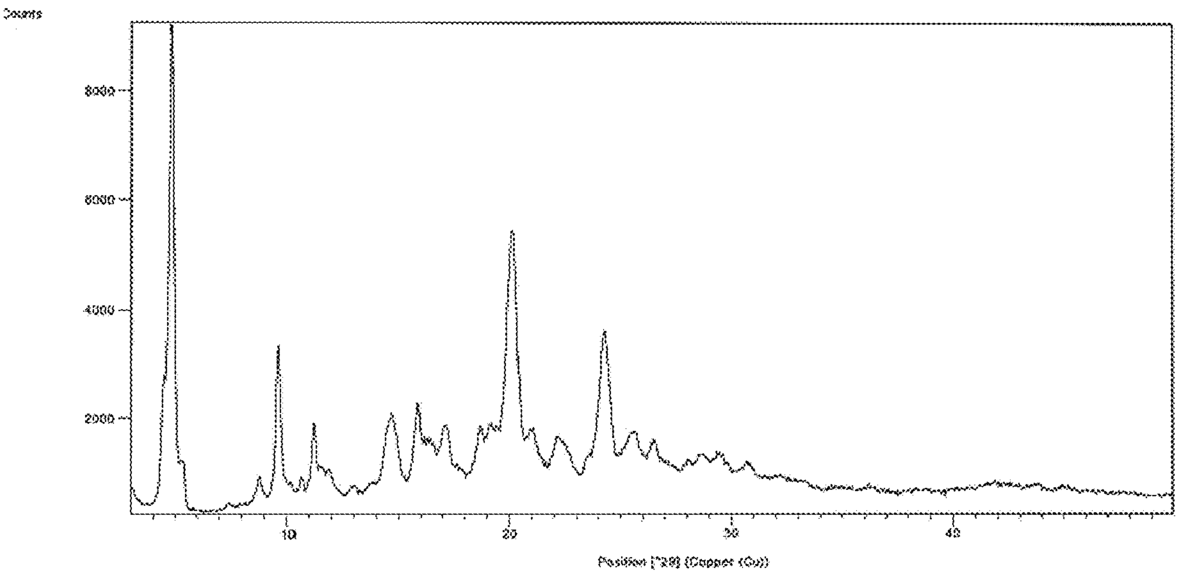
FIG. 7: Illustrates a characteristic PXRD of recrystallized wet compound of Venetoclax obtained according to example-4(c).
Figure 8:
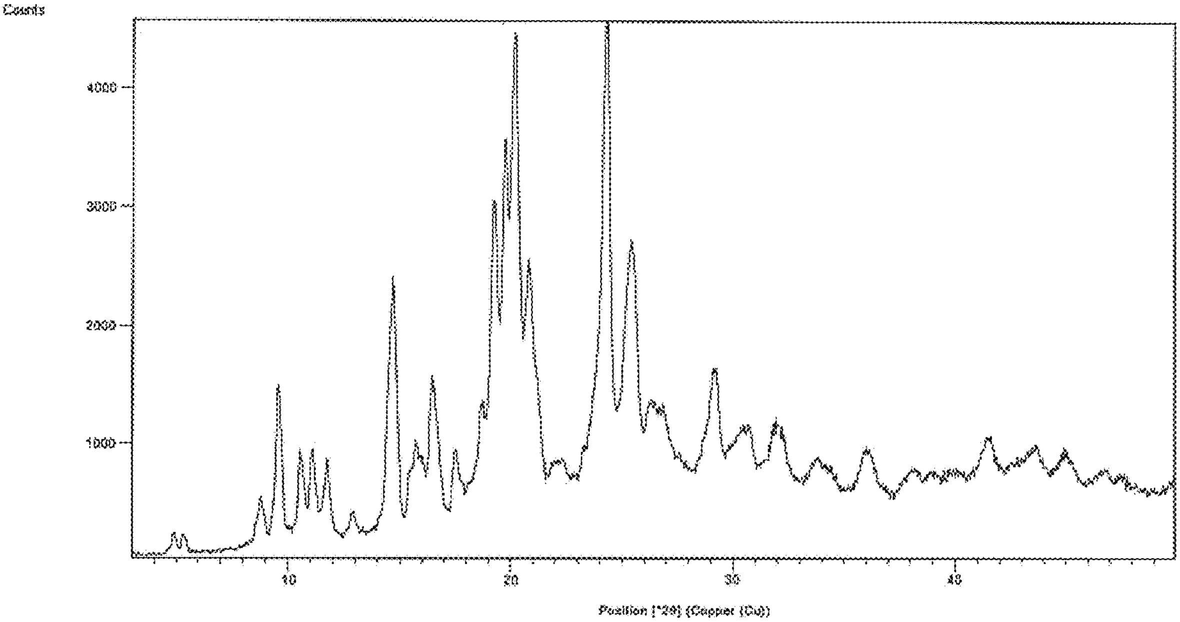
FIG. 8: Illustrates a characteristic PXRD of recrystallized dry compound of Venetoclax obtained according to example-4(c).

The PXRD of recrystallized wet compound of Venetoclax is illustrated in figure-7 and dry compound is illustrated in figure-8.

Example-5: Process for the Preparation of Amorphous Form of Venetoclax Compound of Formula-1

Dimethyl sulfoxide (150 mL) and Venetoclax (50 g) were charged into 4N RB flask and stirred for 20-30 min at 25-30° C. Filtered the reaction mass and washed with dimethyl sulfoxide. Charged water (1500 mL) into another RB flask and cooled to 5-10° C. Added the above filtrate to the pre-cooled water and stirred for 20-30 min at 5-10° C. Filtered and washed the wet compound with water and dried to get the title compound. Yield: 48 g (96% w/w); Purity: 99.84% by HPLC.

We claim:

1. A process for the preparation of Venetoclax formula-1, comprising:

a) Reacting 4-fluoro-2-(1H-pyrrolo[2,3-b]pyridin-5-yloxy)benzoic acid methyl ester (formula-2) with 1-[[2-(4-chlorophenyl)-4,4-dimethyl-cyclohexen-1-yl] methyl]piperazine (formula-3) in the presence of an organic base selected from diisopropylethylamine, triethylamine or mixtures thereof, in dimethylsulfoxide to provide methyl 4-[4-[[2-(4-chlorophenyl)-4,4-dimethyl-cyclohexen-1-yl]methyl]piperazin-1-yl))-2-(1H-pyrrolo[2,3-b]pyridin-5-yloxy) benzoate (formula-4), b) treating the compound obtained in step a) in-situ with aqueous NaOH in dimethylsulfoxide to provide 4-[4-[[2-(4-chlorophenyl)-4,4-dimethyl-cyclohexen-1-yl] methyl]piperazin-1-yl))-2-(1H-pyrrolo[2,3-b]pyridin-5-yloxy)benzoic acid (formula-5), c) reacting the compound of formula-5 with 3-nitro-4-((tetrahydro-2H-pyran-4-yl) methylamino)benzene sulfonamide (formula-6) in the presence of EDC.HCI and DMAP in methylene chloride to provide Venetoclax (formula-1), and d) purifying the Venetoclax (formula-1) by re-crystallisation from toluene to provide a pure compound of formula-1,

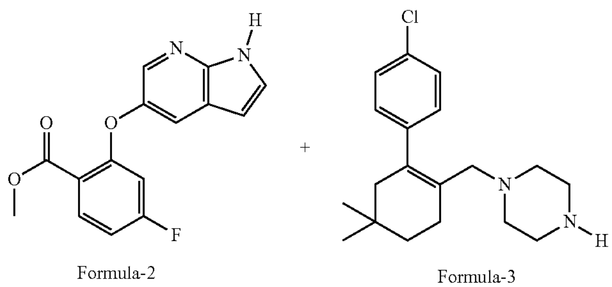

Formula-2

Formula-3

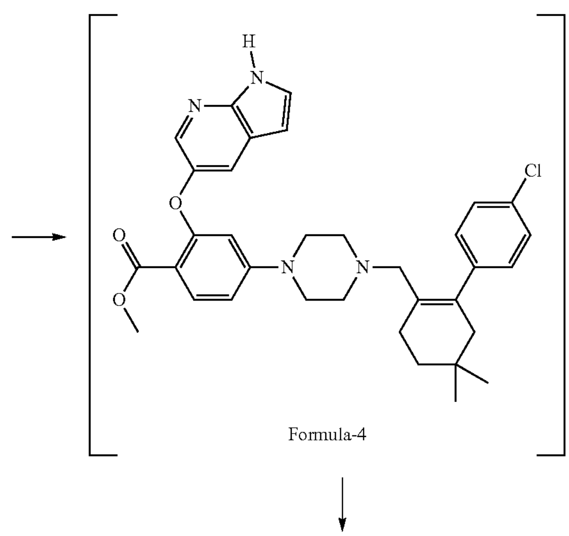

Formula-4

-continued

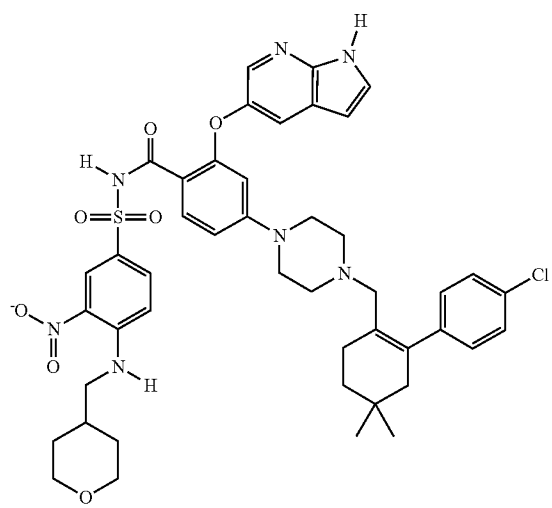

(Venetoelax)
Formula-1

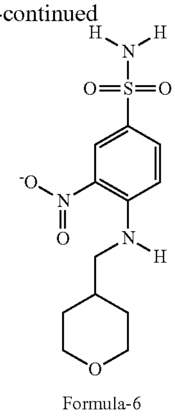

Formula-6

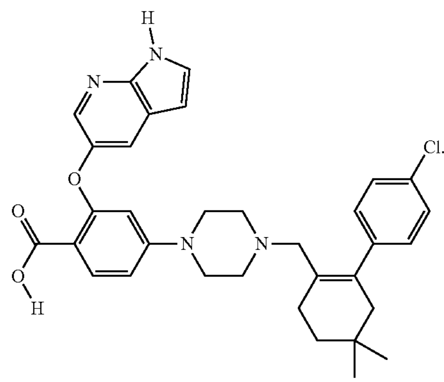

Formula-5

2. The process as claimed in claim 1, wherein, in step-a) the organic base used is triethylamine.

3. A process for the preparation of Venetoclax compound of formula-1, as claimed in claim 1, comprising of:

a) Reacting 4-fluoro-2-(1H-pyrrolo[2,3-b]pyridin-5-yloxy)benzoic acid methyl ester (formula-2) with 1-[[2-(4-chlorophenyl)-4,4-dimethyl-cyclohexen-1-yl] methyl]piperazine (formula-3) in the presence of triethylamine in dimethylsulfoxide to provide methyl 4-[4-[[2-(4-chlorophenyl)-4,4-dimethyl-cyclohexen-1-yl]methyl]piperazin-1-yl))-2-(1H-pyrrolo[2,3-b]pyridin-5-yloxy) benzoate (formula-4), and purifying the obtained compound by re-crystallisation from methanol followed by water, b) treating the compound obtained in step a) in-situ with aqueous NaOH in dimethylsulfoxide to provide 4-[4-[[2-(4-chlorophenyl)-4,4-dimethyl-cyclohexen-1-yl] methyl]piperazin-1-yl))-2-(1H-pyrrolo[2,3-b]pyridin-5-yloxy)benzoic acid (formula-5), and purifying the obtained compound by re-crystallisation from a mixture of toluene and acetonitrile, c) reacting the compound of formula-5 with 3-nitro-4-((tetrahydro-2H-pyran-4-yl) methylamino)benzene sulfonamide (formula-6) in the presence of EDC.HCl and DMAP in methylene chloride to provide Venetoclax (formula-1), and purifying the obtained compound by re-crystallisation from a mixture of toluene and acetonitrile, and d) purifying the Venetoclax (formula-1) by re-crystallisation from toluene to provide a pure compound of formula-1.

4. The process as claimed in claim 1, wherein the purification of Venetoclax (formula-1) in step d) comprises:

a) Adding Venetoclax compound of formula-1 in toluene, b) heating, stirring, cooling and filtering the reaction mixture, c) adding a mixture of toluene and acetonitrile to the filtrate obtained in step-(b), d) heating, stirring, cooling and filtering the reaction mixture, e) adding toluene to the filtrate obtained in step-(d), f) heating, stirring, cooling the reaction mixture, g) filtering, washing and drying the compound obtained in step (f) to get pure Venetoclax (formula-1).

* * * * *